US007371720B2

(12) United States Patent
Ribeiro De Paiva et al.

(10) Patent No.: US 7,371,720 B2
(45) Date of Patent: May 13, 2008

(54) **CATIONIC PEPTIDES OF THE PHYLLOSEPTIN FAMILY ISOLATED FROM THE SKIN SECRETION OF *PHYLLOMEDUSA HYPOCHONDRIALIS***

(75) Inventors: Genaro Ribeiro De Paiva, Brasilia (BR); Carlos Bloch Júnior, Brasilia (BR); José Roberto de Souza De Almeida Leite, Brasilia (BR); Luciano Paulino Da Silva, Taguatinga (BR)

(73) Assignees: Empressa Brasileira de Pesquisa Agropecuaria - Embrapa, Brasilia (BR); Fundacao Universidade de Brasilia, Brasilia (BR)

( * ) Notice: Subject to any disclaimer, the term of this patent is extended or adjusted under 35 U.S.C. 154(b) by 302 days.

(21) Appl. No.: 10/484,837

(22) PCT Filed: Jul. 26, 2002

(86) PCT No.: PCT/BR02/00104

§ 371 (c)(1), (2), (4) Date: Jul. 2, 2004

(87) PCT Pub. No.: WO03/010191

PCT Pub. Date: Feb. 6, 2003

(65) Prior Publication Data

US 2004/0242488 A1 Dec. 2, 2004

(30) Foreign Application Priority Data

Jul. 27, 2001 (BR) .................................. 0104510

(51) Int. Cl.
*A61K 38/02* (2006.01)
*A61K 38/10* (2006.01)

(52) U.S. Cl. ............................................ 514/2; 514/13

(58) Field of Classification Search ..................... None
See application file for complete search history.

(56) References Cited

OTHER PUBLICATIONS

Hancock et al 1999, Antimicrobial Agents and Chemotherapy, vol. 43, No. 6, pp. 1317-1323.*

Cammue et al. 1992, J Biol Chem, vol. 267, No. 4, pp. 2228-2233.*

Hancock, R.E.W., Falla, T., and Brown, M., "Cationic Bactericidal Peptides," *Adv. Microbiol. Physiol.*, 37:135-175 (1995).

Steiner, H. et al., "Sequence and Specificity of Two Antibacterial Proteins Involved in Insect Immunity", Nature, vol. 292, pp. 246-248, (Jul. 16, 1981).

Kagan, B. L. et al., "Antimicrobial Defensin Peptides Form Voltage-Dependent Ion-Permeable Channels in Planar Lipid Bilayer Membranes", Pro. Natl. Acad. Sci. USA, vol. 87, pp. 210-214, (Jan. 1990).

Park, C. B. et al., "A Novel Antimicrobial Peptide from *Bufo bufo gargarizans*", Biochemical and Biophysical Research Communications, vol. 218, pp. 408-413, (1996).

Batista, C. V. F. et al., "Antimicrobial Peptides from the Brazilian frog *Phyllomedusa distincta*", Peptides, vol. 20, pp. 679-686, (1999).

Bello, J. et al., "Conformation and Aggregation of Melittin: Dependence on pH and Concentration", Biochemistry, vol. 21, pp. 461-465, (1982).

Kadono-Okuda, et al., "Effects of Synthetic *Bombyx mori* Cecropin B on the Growth of Plant Pathogenic Bacteria", Journal of Invertebrate Pathology, vol. 65, pp. 309-310, (1995).

Gibson, B. W. et al., "Bombinin-like Peptides with Antimicrobial Activity from Skin Secretions of the Asian Toad, *Bombina orientalis*", The Journal of Biological Chemistry, vol. 266, Issue of Dec. 5, pp. 23103-23111, (1991).

Falla, T. J. et al., "Mode of Action of the Antimicrobial Peptide Indolicidin", The Journal of Biological Chemistry, vol. 271, No. 32, Issue of Aug. 9, pp. 19298-19303, (1996).

Cammue, B. P. A. et al., "Isolation and Characterization of a Novel Class of Plant Antimicrobial Peptides from *Mirabilis jalapa* L. Seeds", The Journal of Biological Chemistry, vol. 267, No. 4, Issue of Feb. 5, pp. 2228-2233, (1992).

Sharma, A. et al., "Transgenic Expression of Cecropin B, an Antibacterial Peptide from *Bombyx mori*, Confers Enhanced Resistance to Bacterial Leaf Blight in Rice", FEBS Letters, vol. 484, pp. 7-11, (2000).

Park, C. B. et al., "Structure-Activity Analysis of Buforin II, a Histone H2A-Derived Antimicrobial Peptide: The Proline Hinge is Responsible for the Cell-Penetrating Ability of Buforin II", PNAS, vol. 97, No. 15, pp. 8245-8250, (Jul. 18, 2000).

Kuzuhara, T. et al., "Determination of the Disulfide Array in Sapecin, an Antibacterial Peptide of *Sacrcophaga peregrina* (Flesh Fly)", J. Biochem., vol. 107, pp. 514-518, (1990).

Zasloff, M., "Magainins, a Class of Antimicrobial Peptides from *Xenopus* Skin: Isolation, Characterization of Two Active Forms, and Partial cDNA Sequence of a Precursor", Proc. Natl. Acad. Sci. USA, vol. 84, pp. 5449-5453, (Aug. 1987).

Westerhoff, H. V. et al., Magainins and the Disruption of Membrane-Linked Free-Energy Transduction, Proc. Natl. Acad. Sci. USA, vol. 86, pp. 6597-6601, (Sep. 1989).

Saberwal, G. et al., "Cell-Lytic and Antibacterial Peptides that Act by Perturbing the Barrier Function of Membranes: Facets of Their Conformational Features, Structure-Function Correlations and Membrane-Perturbing Abilities", Biochimica et Biophysica Acta, vol. 1197, pp. 109-131, (1994).

Daba, H. et al., "Detection and Activity of a Bacteriocin Produced by *Leuconstoc mesenteroides*", Applied and Environmental Microbiology, vol. 57, No. 12, pp. 3450-3455, (Dec. 1991).

(Continued)

*Primary Examiner*—Anish Gupta
*Assistant Examiner*—Ronald T Niebauer
(74) *Attorney, Agent, or Firm*—Finnegan, Henderson, Farabow, Garrett & Dunner, L.L.P.

(57) ABSTRACT

The present invention relates to a class of anti-microbial peptides, called Phyllosepti ns, isolated from *Phyllomedusa hypochondrialis*. The invention also relates to therapeutic and agricultural compositions comprising one or more Phylloseptins. Methods of treating infections of various mammalian organs such as the skin and methods of treating plant infections are also included in the invention.

10 Claims, 4 Drawing Sheets

OTHER PUBLICATIONS

Boman, H. G., "Peptide Antibiotics and Their Role in Innate Immunity", Annu. Rev. Immunol., vol. 13, pp. 61-92, (1995).

Nicolas, P. et al., "Peptides as Weapons Against Microorganisms in the Chemical Defense System of Vertebrates", Annu. Rev. Microbiol., vol. 49, pp. 277-304, (1995).

Hancock, R. E. W. et al., "Minireview: Peptide Antibiotics", Antimicrobial Agents and Chemotherapy, vol. 43, No. 6, pp. 1317-1323, (Jun. 1999).

* cited by examiner

SEQUENCE LISTING

```
<160> NUMBER OF SEQ ID NOS: 4

<210> SEQ ID NO 1
<211> LENGTH: 19
<212> TYPE: PRT
<213> ORGANISM: Phyllomedusa Hypochondrialis

<400> SEQUENCE: 1

Phe Leu Ser Leu Ile Pro His Ala Ile Asn Ala Val Ser Ala Ile Ala
 1               5                  10                  15

Lys His Asn

<210> SEQ ID NO 2
<211> LENGTH: 19
<212> TYPE: PRT
<213> ORGANISM: Phyllomedusa Hypochondrialis

<400> SEQUENCE: 2

Phe Leu Ser Leu Ile Pro His Ala Ile Asn Ala Val Ser Thr Leu Val
 1               5                  10                  15

His His Phe

<210> SEQ ID NO 3
<211> LENGTH: 19
<212> TYPE: PRT
<213> ORGANISM: Phyllomedusa Hypochondrialis

<400> SEQUENCE: 3

Phe Leu Ser Leu Ile Pro His Ala Ile Asn Ala Val Ser Ala Leu Ala
 1               5                  10                  15

Asn His Gly

<210> SEQ ID NO 4
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (14)..(17)
<223> OTHER INFORMATION: Independently a hydrophobic amino acid, a
      hydrophilic
      basic amino acid or a hydrophilic neutral amino acid
<220> FEATURE:
<221> NAME/KEY: MOD_RES
<222> LOCATION: (19)
<223> OTHER INFORMATION: Independently a hydrophobic amino acid, a
      hydrophilic
      basic amino acid or a hydrophilic neutral amino acid
<220> FEATURE:
<223> OTHER INFORMATION: When residues 14, 15 & 16 are hydrophobic amino
```

-continued

```
      acids,
      residue 17 is a hydrophilic basic amino acid and residue
      19 is a hydrophilic neutral amino acid
<220> FEATURE:
<223> OTHER INFORMATION: When residues 15, 16 and 19 are hydrophoic
      amino acids
      residue 14 is a hydrophobic amino acid or a hydrophilic
      neutral amino acid and residue 17 is a hydrophilic basic
      amino acid or a hydrophilic neutral amino acid

<400> SEQUENCE: 4

Phe Leu Ser Leu Ile Pro His Ala Ile Asn Ala Val Ser Xaa Xaa Xaa
  1               5                  10                  15

Xaa His Xaa
```

CATIONIC PEPTIDES OF THE PHYLLOSEPTIN FAMILY ISOLATED FROM THE SKIN SECRETION OF *PHYLLOMEDUSA HYPOCHONDRIALIS*

This application is a national stage application of PCT/BR02/00104, filed on Jul. 26, 2002, which claims priority to Brazilian patent application number PI0104510-5, filed on Jul. 27, 2001.

FIELD OF INVENTION

This invention is related to anti-microbial peptides with activity against a broad range of Gram-negative and Gram-positive bacteria, fungi and protozoa. Pharmaceutical compositions containing the anti-microbial peptides here disclosed are useful to be used in prophylaxis and therapeutic treatment of human and animals under conditions which depress or compromise their immune system. Compositions based on the peptides of the invention are also useful in retarding plant pathogens growth.

BACKGROUND OF THE INVENTION

Bacteria and fungi as well as other organisms, including plant pathogens, coexist with all living organisms and besides this fact, pathogenic infections are not frequent because of the efficiency of self defense mechanisms. Microorganisms that invade the human or animal body and plants are challenged by several defense mechanisms.

When host defenses lacks an efficient barrier against pathogen invasion, antibiotics have been used to function as bactericides and, in general, anti-microbials. However, different antibiotics have been continuously sought due to the severe side-effects and the emergence of mutant microorganisms acquired resistance to the long-term used antibiotics. In this regard, attempts to develop novel antibiotics have been carried out by screening secondary metabolites of microorganisms, by synthesizing analogues of known antibiotics such as quinolones or by isolating proteins or peptides induced by intracellular defense mechanisms of plants and animals.

In fact, host defenses include mechanical and chemical factors. One of the chemical defense mechanisms of animals and plants against infection is the production of peptides that have anti-microbial activity. Naturally occurring amphipathic lytic peptides play an important if not critical role as immunological agents and have some defense functions in a range of animals. The function of these peptides is to destroy prokariotic and other non host cells by disrupting the cell membrane and promoting cell lysis. Common features of these naturally occurring peptides include an overall basic charge, a small size (23-39 amino acid residues) and the ability to form amphiphilic α-helices.

Many different families of anti-microbial peptides, classified by their amino acid sequence and secondary structure have been isolated from insects (Steiner, H.; Hltmark, D.; Engstrom, A.; Bennich, H. & Boman, H. G.,1991. *Nature*.292, 246-248); plants (Cammue, B. P.; De Bolle, M. F.; Terras, F. R.; Proost, P.; Van Danrne, J.; Rees, S. B.; Vanderleyeden, J. and Broekaert, W. F. 1992. *J. Biol. Chem.* 267. 2228-2233.), mammals (Nicolas, P. & Mor, A. .1995. *Annu. Rev. Imunol.* 49: 277-304) and microorganisms (Boman, H. G.1995. *Annu. Rev. Imunol.* 13: 61-92).

Cecropin, cysteine-containing defensin and sapecin, isolated from insects, are examples of antibacterial peptides whose target site is lipid membrane of Gram positive bacteria (Kuzuhara, T. et al. 1990. J. Biochem. 107: 514-518). Studies have demonstrated that Cecropin B isolated from *Bombix mori* have biological activity against bacterial species (Kadono-Okuda, K. Taniai, K., Kato, Y. Kotani, E. & Yamakawa, M. 1995. *J. Invertebr. Pathol.* 65, 309-310). Further, it was reported that this peptide when translocated into the intercellular spaces in rice transgenic plants is protected from degradation by plant peptidases and confers enhanced resistance against *Xanthomonas oryzae* pv. *oryzae* infection (Sharma, A.;, Sharma, R.; Imamura, M.; Yamakawa, M. & Machii, H. 2000. *FEBS*. 484: 7-11).

Attacin, sarcotoxin, deftericin, coleoptericin, apidaecin and abaecin are other antibacterial peptides whose target site are lipid membranes. These peptides conserve G and P domains, and have an influence on the cell differentiation of Gram negative bacteria. In particular, attacin has been also reported to break down outer membrane of the targeted bacteria by inhibiting the synthesis of outer membrane proteins.

Besides the above cited antibacterial peptides of insects, several antibiotic peptides have been also isolated from amphibia. Indeed, as other animals, amphibians are rich in anti-microbial peptides (Zasloff, M. 1987. *Proc. Natl. Acad. Sci.* 89:5449-5453), and many of them belong to the group of amphipathic α-helical structure peptides such as magainins (Daba, H., Pandian, S., Gosselin, J. F. Simard, R. E., Huang, J. and Lacroix, C. 1991. *Appli. Environ. Microbiol.* 57, 3450-3455), bombinins (Gibson, B. W., Tang, D., Mandrell, R., Kelly, M. and Spindel, E. R. 1991. *J. Biol. Chem.* 266, 23103-23111), bufonins (Park, C. B., Kim, M. S. and Kim, S. C. (1996) *Biochem. Biophys. Res. Comm.* 218, 408-413.), dermaseptins (Batista, C. V. C., Silva, L. R., Sebben, A., Scaloni, A., Ferrara, L., Paiva, G. R., Olamendi-Portugal, T., Possani, L. D. and Bloch, C. Jr. 1999. *Peptides* 20, 679-686) and defensins (Kagan, B. L. et al. 1990. "Anti-microbial defensin peptides form voltage-dependent ion-permeable channels in planar lipid bilayer membranes. Proc Natl Acad Sci. USA. 87(1):210-214). Most of these peptides have been isolated from glands and gastrointestinal tract.

All these molecules has been subject of intense research in order to clarify their biosynthesis, mechanism of action, activity towards microorganisms and potential clinical applications.

An important class of anti-microbial peptides are those known as Magainins. According to Zasloff (1987), at least five proteins may be isolated from the skin of the African clawed frog (*Xenopus laevis*). The natural proteins are active against a broad range of microorganisms including bacteria, fungi and protozoans. The broad spectrum anti-microbial activity is also present in synthetic peptides and in certain truncated analogs of the natural proteins. Such a class of broad spectrum bio-active polypeptides have been described in the U.S. Pat. No. 5,643,876. These peptides have a molecular weight of about 2500 Da or less, are highly water soluble, amphiphilic and non-hemolytic. They are also defined as a class of substantially pure, homogeneous peptide composed of about 25 amino acids.

The U.S. Pat. No. 5,424,395 discloses a synthetic peptide with 23 amino acid, derived from magainin II showing anti-microbial activity in plants. U.S. Pat. No. 5,912,231 presents a compound comprising a Magainin I or a Magainin II peptide with biological activity, wherein at least one substitution may be made for certain amino acid residues with other amino acids residues. The resulting peptides are known as substitution analogues. Preferred peptides are those obtained by deletion or substitution of at least one amino acid residue in the position 15 andor 23.

U.S. Pat. No. 5,424,395 also describes synthetic peptides derived from Magainin I and Magainin II having anti-microbial activity. The peptides contain 23 amino acid residues and are useful in retarding the growth of plant pathogens.

U.S. Pat. No. 5,912,230 discloses an invention based on substantially pure peptides which have anti-candidal or anti-bacterial activity which are equivalent to that of naturally occurring histatins but are smaller in size. These peptides represent defined portions of the amino acid sequences of naturally occurring human histidine-rich salivary proteins called histatins.

Defensins are relatively small polypeptides of about 3-4 kDa, rich in cysteine and arginine. As a class of anti-microbial peptides, defensins have activity against some bacteria fungi and viruses. The defensins are believed to have molecular conformations stabilized by cysteine bonds, which are essential for biological activity.

The documents U.S. Pat. No. 5,861,378 and U.S. Pat. No. 5,610,139 disclose peptides isolated from horseshoe crab hemocyte, having a similar amino acid sequence to those of defensin and showing strong anti-microbial activities in the fraction 5S, as well as compositions and pharmaceutical preparations using them. They also provide a DNA encoding one or more peptides which show significant physiological activity against Gram positive and Gram negative bacteria and fungi. U.S. Pat. No. 5,610,139 also presents antimicrobial compositions, containing the referred peptides combined with one or more β-lactol or chloramphenicol antibiotics, these compositions exihibing synergistic bactericidal effect against *S. aureus* infections.

In the U.S. Pat. No. 5,766,624 is proposed a method for treatment of microbe infection in mammals using defensins; U.S. Pat. No. 5,821,224 also presents a β-defensin of 38-42 amino acid, with anti-microbial activity, obtained from bovine neutrophil.

Cathepsin G is a granule protein with chymotripsin-like activity being also known as chymotripsin-like cationic protein. Some polypeptides mutually homologous to cathepsin G are called defensins. In the U.S. Pat. No. 5,798,336 various peptides with anti-microbial activity are provided, being the sequence of said peptides related to amino acid sequences within Cathepsin G. Despite of some of the peptides have showed specificity because of being more effective against determined microorganism, mostly they were effective against both, Gram-negative and Gram-positive bacteria. It is mentioned that pharmaceutical compositions containing these peptides are useful in prophylaxis treatment of infections.

Another type of anti-microbial peptides named buforin was isolated from the stomach tissue of the Asian toad *Bufo bufo garugrizans*. Two molecules derived from histone H2A were identified, Buforin I and Buforin II which contain 39-aa and 21-aa respectively. These molecules showed different mechanisms of action, having buforin II much stronger anti-microbial activity, killing bacteria without lysing cells and presenting high affinity for DNA and RNA. This suggests that the target of this peptide is the nucleic acids and not the cell membranes (see Park, C. B.; Yi, K.; Matsuzaki, K.; Kim, M. S.; Kim, S. C. 2000. *PNAS*. 97:8245-8250).

U.S. Pat. No. 5,877,274 provides a novel class of cationic peptides referred to as bactolysins, which have anti-microbial activity and have the ability to significantly reduce the level of lipopolysaccharide (LPS)-induced tumor necrosis factor (TNF). In this document, it is also proposed a method of inhibiting either the growth of bacteria or an endotoxernia or sepsis associated disorder by administering a therapeutically effective amount of the peptide.

Each one of these different peptide types is distinguished by sequence and secondary structure characteristics. Based only on the sequence, it is difficult to predict either the activity of a peptide or the secondary structure that it will be formed (Hancock, R. E. W., and Chapple, D. S. 1999. *Anti-microbial Agents and Chemotherapy*. 43, 1317-1323).

Most of the peptides without disulfide bridges have random structures in water, and when they bind to a membrane or other hydrophobic environment, or, self-aggregate, they form a structure (Bello, J., Bello, H. R., and Granados, E. 1982. *Biochemistry* 21, 461-465; Falla, T. J., Karunaratne, D. N., and Hancock, R. E. W. 1996. *J. Biol. Chem*. 271, 19298-19303). For example, cecropins and mellitin only acquire amphiphilic alpha-helices in membranous environments. It is known that the both dual cationic and hydrophobic nature of the peptides is important for the initial interaction between the peptide and that is the cationic character of the bacterial membrane what promotes interaction with bacterial outer and cytoplasmic membranes (Hancock, R. E. W., Falla, T., and Brown, M. H. 1995. *Adv. Microb. Physio*. 37, 135-175).

Several hypotheses have been suggested for the mechanism of action of the lytic peptides, most of them related to membrane destruction. Whatever the mechanism of lytic peptide-induced membrane damage, an ordered secondary conformation such as an amphiphilic helix and positive charge density are supposed to participate in the peptide-promoted lysis reaction.

Membrane-binding is the first step of the peptide-membrane interaction V mechanism and the knowledge of its determinants and driving force are prerequisites for understanding the mechanism itself and the molecular reasons for the prokaryotic specificity (Saberwal, G., and Nagaraj, R. 1994. *Biochem. Biophys. Acta* 1197, 109-131). The positively charged peptides were found to bind preferentially to negatively charged membranes what is a major reason for the prokaryotic specificity. The enhanced affinity is caused by an electrostatic attraction of the peptides to the negatively charged membrane surface rather than a specific-lipid interaction (Westerhoff, H. V., Juretic, D., Hendler, R. W., and Zasloff, M. (1989) *Proc. Natl. Acad. Sci. USA*. 86, 6597-6601).

The present invention discloses a novel class of anti-microbial peptide, isolated from skin of *Phyllomedusa hypochondrialis*, a kind of frog native to Amazonian, Brazil. It was termed Phylloseptins and its structure did not show any homology with another known peptides.

SUMMARY OF THE INVENTION

This invention is related to anti-microbial peptides having the same amino acid sequence and at least the same anti-microbial activity as those of Phylloseptins which are isolated from the skin of *Phyllomedusa hypochondrialis*. The peptides did not have any structural homology with another known peptide. The 19-residue anti-microbial peptides are cationic and based on their primary structure, all peptides can be fitted to an amphiphilic α-helix. The peptide masses analyzed by mass spectrometry were in the range of 1.9 to 2.0 kDa. Preferred peptides of the present invention include the peptides named Phylloseptin-I, Phylloseptin-II and Phylloseptin-III which are defined by their amino acid sequence SEQ ID No. 1, SEQ ID No. 2 and SEQ ID No. 3.

The amphiphilic nature of these peptides presumably underlines their biological activities which enables them to associate with lipid membranes and disrupt normal membrane function. However, no significant hemolytic activity was found for these peptides which suggests a selectivity for prokaryotic over eukaryotic membranes A first embodiment of the present invention refers to an antibiotic peptide with broad spectrum anti-microbial activity having the same amino acid sequence and at least the same anti-microbial activity as the peptide defined in the formula:

Phe Leu Ser Leu Ile Pro His Ala Ile Asn Ala Val Ser Xaa$^1$ Xaa$^2$ Xaa$^3$ Xaa$^4$ His Xaa$^5$ (SEQ ID NO: 4) wherein Xaa$^1$, Xaa$^2$, Xaa$^3$, Xaa$^4$ and Xaa$^5$ are each independently a hydrophobic amino acid, a hydrophilic basic amino acid or a hydrophilic neutral amino acid, with the provisos that (i) when Xaa$^1$, Xaa$^2$ and Xaa$^3$ are hydrophobic amino acids, Xaa$^4$ is a hydrophilic basic amino acid and Xaa$^5$ is a hydrophilic neutral amino acid; (ii) when Xaa$^2$, Xaa$^3$ and Xaa$^5$ are hydrophobic amino acids, Xaa$^1$ is hydrophobic amino acid or a hydrophilic neutral amino acid and Xaa$^4$ is a hydrophilic basic amino acid or a hydrophilic neutral amino acid.

A second embodiment is directed to a composition for inhibiting growth of a target cell e.g. fungus, bacteria, protozoa, comprising (a) at least one antibiotic peptide as defined in claim 1 and (b) an acceptable pharmaceutical carrier.

A third embodiment refers to a composition for retarding plant pathogens and for protecting plants from pathogens, comprising (a) at least one antibiotic peptide as defined in claim 1 and (b) an agriculturally acceptable carrier.

A further embodiment of the invention is to provide therapeutic compositions suitable for human, veterinary, or pharmaceutical use, comprising one or more of the peptides released in this invention and an adequate pharmacological carrier.

Preferred peptides of the present invention include the peptides named Phylloseptin-I (PSI), Phylloseptin-II (PSI) and Phylloseptin-III (PSIII) which are defined by their amino acid sequence SEQ ID No. 1, SEQ ID No. 2 and SEQ ID No. 3, respectively.

SEQ ID No. 1:
Phe Leu Ser Leu Ile Pro His Ala Ile Asn Ala Val Ser Ala Ile Ala Lys His Asn

SEQ ID No. 2:
Phe Leu Ser Leu Ile Pro His Ala Ile Asn Ala Val Ser Thr Leu Val His His Phe

SEQ ID No. 3:
Phe Leu Ser Ueu Ile Pro His Ala Ile Asn Ala Val Ser Ala Leu Ala Asn His Gly

DETAILED DESCRIPTION OF THE INVENTION

Figure 1:
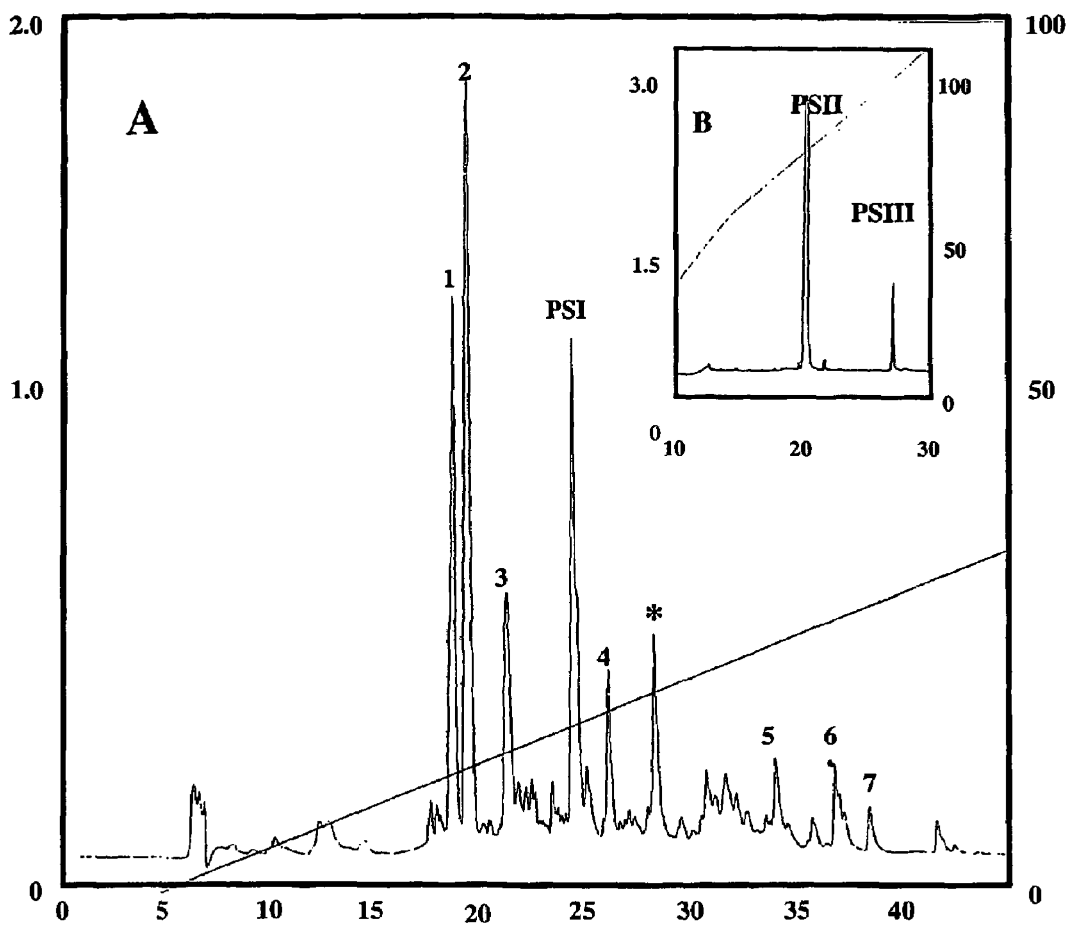
FIG. 1: shows the chromatographic display of the crude extract of skin secretion of *Phyllomedusa hypochondrialis* (A) and the peptides Phylloseptin I (PS1), Phylloseptin II (PS2) after the rechromatographic procedure (B).

For purposes of clarity and a complete understanding of the invention, the following terms are defined "Anti-microbial" refers to peptides that inhibit, prevent, or destroy the growth or proliferation of microbes such as bacteria, fungi, protozoa, or the like.

"Anti-bacterial" is used to mean the peptides which produce effects adverse to the normal biological functions of bacteria, including death or destruction and prevention of the growth or proliferation of the bacteria when contacted with the peptides of the present invention.

"Antibiotic" means the peptides which are unfavorable to the normal biological functions of the non-host cell, tissue, or organism when contacted with the peptides of the present invention.

"Anti-fungal" means the peptides which inhibit, prevent, or destroy the growth or proliferation of fungi.

"Anti-parasitic" refers to peptides which inhibit, prevent, or destroy the growth or proliferation of parasites.

"Anti-infection effective amount" of a pharmaceutical composition means any amount of a pharmaceutical composition which is effective to inhibit or prevent the establishment, growth or spread of an infection sensitive to the peptides of the invention.

"Plant pathogen" encompasses those organisms that can cause damage and/or disease to plants, and includes fungi, prokaryotes (bacteria and mycoplasma), nematodes, protozoa, and the like.

The skins of the South American *Phyllomedusa* frogs are an excellent source of peptide molecules (see Bevins, C. L., Zasloff M. 1990. *Annu. Rev. Biochem*. 59, 295-414; Batista et al. 1999). *Phyllomedusa hypochondrialis* (Anura, *Hylidae*) is an arboreal. frog native to Amazonian, Brazil.

The present invention relates to a novel class of biologically active peptides named Phylloseptins. More particularly, this invention provide three new peptides named Phylloseptin-I (PSI), Phylloseptin-II (PSII) and Phylloseptin-III (PSIII), isolated from the skin of adults of *Phyllomedusa hypochondrialis.*

In order to identify and characterize PSI, PSII and PSIII peptides were isolated by fractionation of the total skin secretion of the lyophilized crude extract from *P. hypochondrialis*. The techniques used to isolate the components of such extracts are well known to the skilled artisans and is not a critical feature of the present invention. To illustrate, the isolation of PSI, PSII and PSIII was performed by application (5-mg aliquots each time) of the crude extract to a semi-preparative Vydac reverse-phase chromatographic column, $C_{18}$, 10μ (10×250 mm) in system HPLC. Peptides were purified by using a double linear gradient, initially 0% to 80% acetonitrile containing 0.1% TFA (trifluoacetic Acid) for 70 min, followed by 80% to 100% of same solvent for 20 min. The experiment was monitored 216 nm and fractions were collected manually and lyophilized. The isolated fractions were re-chromatographed by using a Vydac 218 TP 54, $C_{18}$, 5μ (0.46×25 cm), with optimized gradients of acetonitrile in 0.1% TFA over 60 min and their purity was monitored by mas spectrometry (MALDI/TOF).

FIG. 1 shows the chromatographic display of the crude extract (A) and the peptides Phylloseptin II (PSII), Phylloseptin III (PSIIUI) after the rechromatographic procedure (B).

Figure 2:
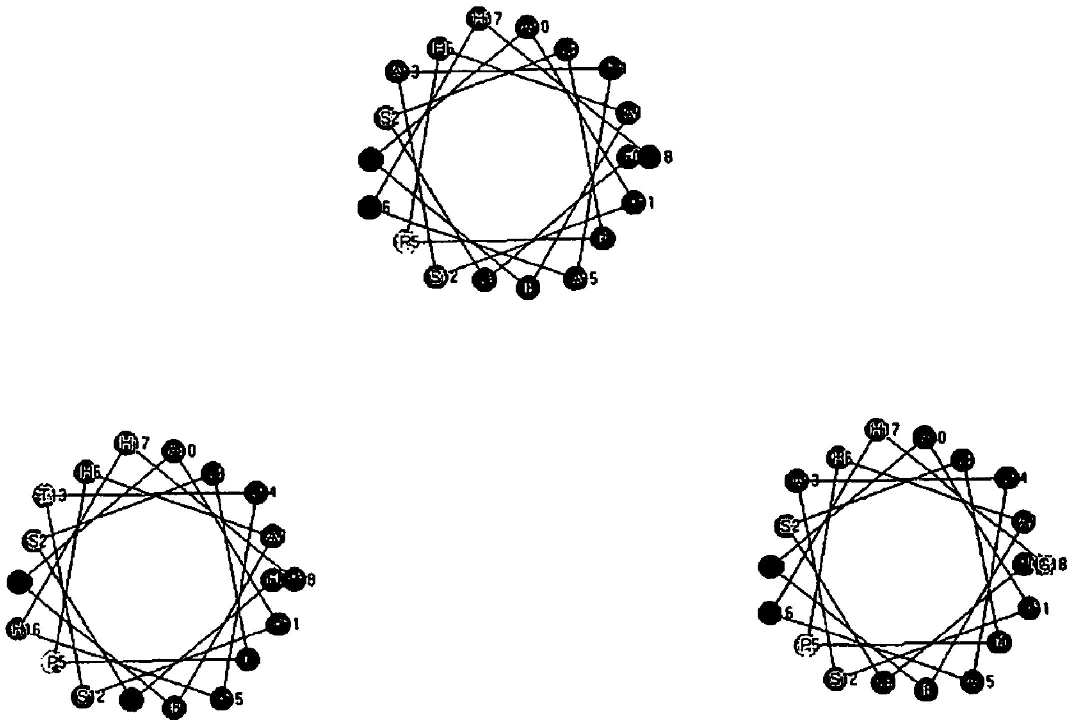
FIG. 2: shows the helical wheel, plots of the Phylloseptins and their amphiphilic structure.
Figure 3:
FIG. 3: shows an AFM image of intact morphological structure of *Pseudomonas aeruginosa.*

The helical wheel plots of the Phylloseptins showing their amphiphilic structure is illustrated in the FIG. 2. In this conformation, periodic variation in the hydrophobicity value of the residues along the peptide backbone with a 3.6 residues/cycle period characterize an α-helix (Schiffer, M. and Edmunson, A. B. 1967. "Use of helical wheels to represent the structures of proteins and to identify segments with helical potential". *Biophys J.* 7(2): 121-35).

The cationic molecules of this invention are unstructured in solution and they could be initially attracted to bacterial surface by electrostatic interactions with negatively charged species (phospholipid heads) on their surface. Then they assume an amphipathic α-helical structure at the membrane surface by inserting the hydrophobic sector into the membrane, in contact with the lipids chains, while polar or, charged residues on the hydrophilic sector remain in contact with the anionic head groups of phospholipids and the outside environment. They thus accumulate on the outer leaflet of membrane with their axis parallel to its surface, causing deformation and thinning.

The antibiotic peptide sequences of the present invention can be composed by either α-D- and/or α-L-amino acid residues in the complete polypeptide chain or specific parts of it (e.g. N-terminal, C-terminal or internal helical regions).

The 19-residue anti-microbial peptides are cationic and based on their primary structure, all three peptides can be fitted to an amphiphilic α-helix. The peptide masses analyzed by mass spectrometry were in the range of 1.9 to 2.0 kDa.

These peptides showed effective activity against a broad range of Gram-negative and Gram-positive bacteria and fungi, However, no significant hemolytic activity was found for these peptides which suggests a selectivity for prokaryotic over eukaryotic membranes.

The term isolated as used herein refers to a peptide substantially free of proteins, lipids, nucleic acid, for examples. Those of skill in the art can make similar substitutions to achieve peptides with the same anti-microbial activity as the peptides of the invention.

The peptides of this invention may be produced by known techniques and obtained in substantially pure form. For example, the peptides may be synthesized manually or on an automatic peptide synthesizer. It is also possible to produce the peptides by genetic engineering techniques. The codons encoding specific amino acids are known to those skilled in the art, and therefore DNA encoding the peptides may be constructed by appropriate techniques, and one may clone such DNA into an appropriate expression vehicle (e.g., a plasmid or a phage) which is transfected into a suitable system for expression of the peptides.

As mentioned before, the peptides of the present invention have a broad range of potent antibiotic activity against a plurality of microorganisms including Gram positive and Gram negative bacteria, fungi, protozoa and other parasites that are harmful to animals, including human, and plants.

Concerning animal prophylaxis and therapeutic treatment, the peptides of the present invention may be employed in promoting or stimulating healing of a wound in a host. The wound healing involves several aspects which include, but are not limited to, increased contraction of the wound, increased deposition of connective tissue, as evidenced by, for example, increased deposition of collagen in the wound, and increased tensile strength of the wound. In short, the peptides of the present invention work as to reverse the inhibition of wound healing caused by conditions which depress or compromise the immune system. Their wound healing activity includes the treatment of external burns and to treat and/or prevent skin and burn infections. In particular, the peptides may be used to treat skin infections caused by Gram positive and/or Gram negative bacteria, such as *P. aeruginosa* and *S. aureus.*

The peptides of the invention also have prophylactic and therapeutic properties concerning eye infections which may be caused by bacteria such as *P. aeruginosa, S. aureus* and *N. gonorrhoeae*, by fungi such as *P. braziliensis, C. albicans* and *A. fumigatus*, by parasites such as *A. casreliani*, or by protozoa.

The peptides of the present invention or analogues thereof may be administered in combination with a non-toxic pharmaceutical carrier or vehicle such as filler, non-toxic buffer, or physiological saline solution. Such pharmaceutical compositions may be used topically or systemically and may be in any suitable form such as liquid, solid, semi-solid, injectable solution, tablet, ointment, lotion, paste, capsule, or the like. The peptide compositions of the present invention may also be used in combination with adjuvants, protease inhibitors, or compatible drugs where such a combination is seen to be desirable or advantageous in controlling infection caused by pathogenic microorganisms including protozoa, and the like, as well as by parasites.

Depending on the use, a composition in accordance with the invention will contain an effective anti-microbial amount and/or an effective antifungal amount and/or an effective anti-parasitic amount and/or an effective antibiotic amount of one or more of the peptides of the present invention.

The peptides disclosed in the present invention may be used in compositions containing other peptides having anti-microbial activity. Examples of these peptides are mentioned in Park, C. B. et al. "Structure-activity analysis of buforin II, a histone H2A-derived antimicrobial peptide: The proline hinge is responsible for the cell-penetrating ability of buforin II" *PNAS.* 97(15), pp. 8245-8250. 2000 and those described the patents U.S. Pat. No. 5,424,395, U.S. Pat. No. 5,912,230, U.S. Pat. No. 5,861,378, U.S. Pat. No. 5,610,139, U.S. Pat. No. 5,821,224 and U.S. Pat. No. 5,877,274.

Referring to the administration form, the peptide compositions of the present invention may be administered by direct application of the peptides to the target cell, or indirectly applied through systemic administration.

Methods of administering pharmaceutical compositions to animals include intravenous, intra-arterial, intra-ocular, intra-peritoneal, intramuscular, intra-nasal, intra-vaginal, subcutaneous, rectal and topical administration. The mode of administration chosen for a particular pharmaceutical composition will depend upon a number of factors well known to the ordinarily skilled artisan or well within his purview to determine without undue experimentation. These include, but are not limited to the treatment subject and its age, size and general condition; the active agent being administered; and the disease, disorder or condition being treated.

Typically, the anti-infection effective of the pharmaceutical compositions provided herein is an amount containing between about 0,1 mg to about 1000,0 mg of one or more of the peptides of the invention per kg of the body weight of the animal to which the composition is administered. Within this range, the amount or dose of the pharmaceutical composition given a particular animal will depend upon a number of factors well known to the skilled person in the art. The particular amount of the pharmaceutical composition administered for the particular disease, disorder or condition indicated may be determined by methods well known to the skilled artisan, e.g., by dose ranging trials.

The peptides, when used in topical compositions, are generally present in an amount of at least 0.1%, by weight.

In such pharmaceutical preparations, amounts greater than 2.0%, by weight are common.

In employing systemically administered compositions, such as intramuscular, intravenous, intraperitoneal, the peptide or peptides of the invention are present in an amount to achieve a serum level of peptide(s) of at least about 5 μg/ml. In most cases, the serum level need not exceed 500 μg/ml. Such serum levels, may be achieved by incorporating the peptide in a composition to be administered systemically at a dose of from 1 to about 100 mg/kg.

In another embodiment, the peptides of the present invention are useful for retarding plant pathogens, and for protecting plants from plant pathogens. In external application, the peptides may, be diluted in liquid solutions or suspensions, or mixed with a solid diluter to be applied as a dust to give a composition containing an amount of between about 1 to abort 100 μg of one or more peptides of the invention. Detailed methods for adapting general methods of application to specific crops and pathogens were disclosed in *Methods for evaluating pesticides for control of plant pathogens*. Hickey, K. D., Ed., The American Phytopathological Society (St. Paul, Minn.), 1986. Methods of application that are expected to be particularly useful in accordance with this aspect of the present invention include intermittent aqueous and non-aqueous sprays of the entire plant or parts thereof, seed coatings, and inclusion in irrigation systems (e.g., green-house mist-benches). Adjuncts that could be added to the formulation would include agents to aid solubilization, wetting agents and stabilizers, or agents that would produce microencapsulated product.

The present invention will be further described with respect to the examples as follows, but the scope of the invention is not to be limited thereby.

EXAMPLES

Example 1

Peptide Purification

Frog skin secretion (crude extract) was obtained from adult specimens of *Phyllomedusa hypochondralis* captured in Brasilia, Brazil. Frog secretion was obtained by moderate electric estimulation of the skin granular glands of *P. hypochondrialis* and freshly collected in distilled water as a crude extract. The extract was filtered by gravity through filter paper, frozen and lyophilized (Centrivap Concentrador LABCONCO). Peptides separation was performed by application (5-mg aliquots each time) of the crude extract to a semi-preparative Vydac reverse-phase chromatographic column, $C_{18}$, 10μ (10×250 mm) in system HPLC. Peptides were purified by using a double linear gradient, initially 0% to 80% acetonitrile containing 0.1% TFA (trifluoacetic Acid) for 70 min, followed by 80% to 100% of same solvent for 20 min. The experiment was monitored 216 nm and fractions were collected manually and lyophilized. The isolated fractions were re-chromatographed by using a Vydac 218 TP 54, $C_{18}$, 5μ (0.46×25 cm), with optimized gradients of acetonitrile in 0.1% TFA over 60 min and their purity was monitored by mass spectrometry (MALDI/TOF).

The chromatrographic profile correspondent to the total skin secretion of *P. hypochondrialis* after RP-HLPC purification is showed in the FIG. 1A. Peaks 1 to 7 correspond to other bioactive molecules which are not included in the present invention. PSI (Phyloseptin I) is assigned directly on the profile and the component marked with the asterisk (*) corresponds to the mixture of PSII and PSIII; which were individually separated as shown on the insert 1B.

Example 2

Molecular Weight Determination and N-terminal Amino Acid Sequencing

The molecular mass of the anti-microbial peptides was determined by MALDI-TOF (Matrix-Assisted Laser Desorption/Ionization—Time Of Flight) mass spectrometry. Individual peptides were mass analyzed in a Voyager DE-STR MALDI-TOF mass spectrometer (PerSeptive Biosystems). Approximately 5 pmol of lyophilized peptide dissolved in distilled water was mixed with a saturated solution of α-cyano-4-hydroxycinnarnic acid. The experiment was carried out under reflector mode for monoisotopic resolution. Data were processed using, GRAMS V. 4.30 (Galactic Software). All spectra were obtained with close internal calibration using Sequazyme PerSeptive Biosystems molecular mass standards.

Amino acid sequencing was performed by the automated Edman degradation method on an PPSQ-23 Protein Peptide Sequencer SHIMADZU and the pairwise and multiple sequence alignment among sequences, were determined by using CLUSTAL V multiple sequence alignment software.

TABLE 1

Maximized pairwise and multiple sequence alignments of Phylloseptins I, II and III. (SEQ ID NOS 1, 2, 1, 3, 2, 3, 1, 2 and 3, respectively in order of appearance)

| PEPTIDE | | SIMILARITY |
|---|---|---|
| PS I | FLSLIPHAINAVSAIAKHN | 74% |
| PS II | FLSLIPHAINAVSTLVHHF | |
| | *************    * | |
| PS I | FLSLIPHAINAVSAIAKHN | 84% |
| PS III | FLSLIPHAINAVSALANHG | |
| | ************** * * | |
| PS II | FLSLIPHAINAVSTLVHHF | 79% |
| PS III | FLSLIPHAINAVSALANHG | |
| | ************* *  * | |
| PS I | FLSLIPHAINAVSAIAKHN | 74% |
| PS II | FLSLIPHAINAVSTLVHHF | |
| PS III | FLSLIPHAINAVSALANHG | |
| | *************     * | |

Example 3

Hemolysis Assay

Human erythrocytes (blood type $O^-$) from a 25-year-old healthy male were freshly prepared prior to each experiment. Hemolytic activity was assayed as described by Aboudy etal (Aboudy, Y., Mendelson, E., Shalit, I., Bessalle, R., Fridikin, M. 1994. *Int. J. Peptide Protein Res*. 43, 573-582.) with minor modifications. Three milliliters of freshly prepared erythrocytes (for methodology see Gibson, B. W., Tang, D., Mandrell, R., Kelly, M. and Spindel, E. R. 1991. *J. Biol. Chem*. 266, 23103-23111.21) was washed with isotonic phosphate-buffered saline (PBS), pH 7.4, until the color of the supernatant turned clear. The washed erythrocytes were then diluted to a final volume of 20 ml in the same buffer. Aliquots of cell suspentions (190 μl) containing samples (10 μl) were serially diluted in PBS, incubated at 37° C. for 30 min and then centrifuged at 4000×g for 5 min; 100 μl of supernatant was taken, diluted to 1.0 ml with PBS, and monitored at 567 nm. The relative optical density, as compared with that of the cell suspension treated with 0.2% Triton X-100, was defined as % hemolysis.

The hemolytic activity of Phylloseptin I and II was tested at different concentrations. The results are showed in Table 2.

TABLE 2

Hemolytic activities of Phylloseptin I (PS I) and Phylloseptin II (PS II).

| Concentrations | | % Hemolysis of human red blood cells | |
|---|---|---|---|
| μg/mL | μM | PS I | PS II |
| 1 | 0.496 | 0.00 | 0.00 |
| 2 | 0.990 | 0.00 | 0.00 |
| 4 | 1.980 | 0.00 | 0.10 |
| 8 | 3.968 | 0.30 | 0.28 |
| 16 | 7.937 | 0.57 | 0.70 |
| 32 | 15.873 | 0.60 | 0.80 |
| 64 | 31.746 | 0.98 | 1.05 |
| 128 | 63.492 | 1.98 | 2.05 |

Example 4

Anti-microbial Assay

The microorganisms *Escherichia coli* ATTC 25922, *Pseudomonas aeroginosa* ATTC 27853, *Staphylococcus aureus* ATTC 25923 and *Enterococcus faecalis* ATTC 29212 and a Brazilian strain of *P. aeroginosa* were used for the anti-microbial assay The microorganisms were cultured in stationary culture at 37° C. Bacteria were grown in Tryptic Soy Broth (TSB). The bioassays were performed by liquid growth inhibition assay lawn as described by Bulet et al (Bulet, P., Dimarcq, J. L., Hetru, C., Lagueux, M., Charlet, M., Hegy, G., VanDorsselaer, A. and Hoffmann, J. A. 1993. *J. Biol. Chem.* 268, 14893-14897). Molecules of Phylloseptin I were dissolved in sterile distilled and deionized water and diluted 8-fold in TSB (OXIOD England) broth. Various concentrations of PSI solution were tested, being the highest 128 μg/ml. The initial inoculum was approximately $1\times10^5$ colony forming units (CFU)/ml and limit of detection was $10^2$ CFU/ml. The final volume was 250 μl (25 μl of the peptide test in water, 25 μl of the inoculum in TSB, and 200 μl of TSB broth). The minimal inhibitory concentration (MIC) was measured for turbidity (OD at 595 nm) 20 h after all microorganisms were grown in stationary culture at 37° C. The lowest concentration of the peptide in which no growth occurred was defined as the MIC.

The minimal inhibitory concentrations (MICs) of the isolated Phylloseptin I against several Gram-positive and Gram-negative bacteria were determined as described by Park et al (Park, C. B., Kim, M. S., and Kim, S. C. 1996. 218 *Biochem. Biophys. Res. Commun.* 408-413.). The lowest concentration of anti-microbial peptide which showed visible suppression of growth was defined as the MIC. That is, the minimal inhibitory concentration was defined as the peptide concentration which produces 100% of microorganism growth inhibition after 20 h incubation in culture media. The results are showed in Table 3.

TABLE 3

Antibacterial activity of PS I defined by criteria of minimal inhibitory concentration.

| Bacteria | Minimal Inhibitory concentration | | | | |
|---|---|---|---|---|---|
| | PS I | Chloranfenicol | Gentamicyn | Amplicilyn | Polimixyn B |
| | μg/mL | | | | |
| *Pseudomonas aeruginosa* wt | 6 | — | 64 | — | 16 |
| *Staphilococcus aureus* ATTC | 16 | 32 | — | — | — |
| *Pseudomonas aeruginosa* ATTC | 8 | — | 64 | — | 16 |
| *Escherichia coli* ATTC | 16 | 32 | 64 | 64 | 64 |
| *Enterococcus faecalis* ATTC | 8 | 32 | — | 128 | — |

(—) there was no inhibition of bacteria proliferation on these concentrations.

Example 5

Determination of Peptide-induced Membrane Alterations by Atomic Force Microscopy Atomic force microscopy (AFM) used in this experiment was a TopoMetrix 2000 Explorer (TopoMetrix, Santa Clara, Calif., U.S.A) operating in the contact mode and at ambient air. A piezoelectric hybrid tube scanner with a maximum scanning area of 50 microns square was used. Standard 200 microns V-shaped $Si_3N_4$ cantilevers with integrated pyramidal tips was used. The nominal spring constant for the contact force of the tip on the specimen surface was set to 0.00 nA. The line scan speed was set to 20 μm/s. *Pseudomonas aeruginosa* ATTC 27853 was used in this experiment. The strain was cultured in nutrient broth at 37° C. for about 12 hours. The bacterial was collected and suspended in 150 mM KCl/20 mM $MgCl_2$/10 mM Tris-HCl, pH 7.8. The concentration of the bacteria in the suspension was adjusted to approximately $4\times10^8$ bacteria/ml according to its turbidity. The bacterial suspension was placed on freshly cleaved mica and air dried. The mica was fixed on the specimen holder with a two-sided adhesive tape and was then installed on the top of the scanner for AFM observation.

AFM has been used extensively to study materials (Lacava, B. M., Azevedo, R. B., Silva, L. P., Lacava, Z. G. M., Skeff Neto, K., Buske, N., Bakuzis, A. F., and Morais, P. C. 2000. *Applied Physics Letter* 77 (12):1876-1878.) and biological samples being considered to be a useful tool for identifying bacterial surface characteristics. AFM has also been used to detect topographic surfaces while operating under determined physiological conditions (Braga, P. C., and Ricci, D. 1998. *Anti-microbial Agents and Chemotherapy* 42 (1):18-22).

Figure 4:
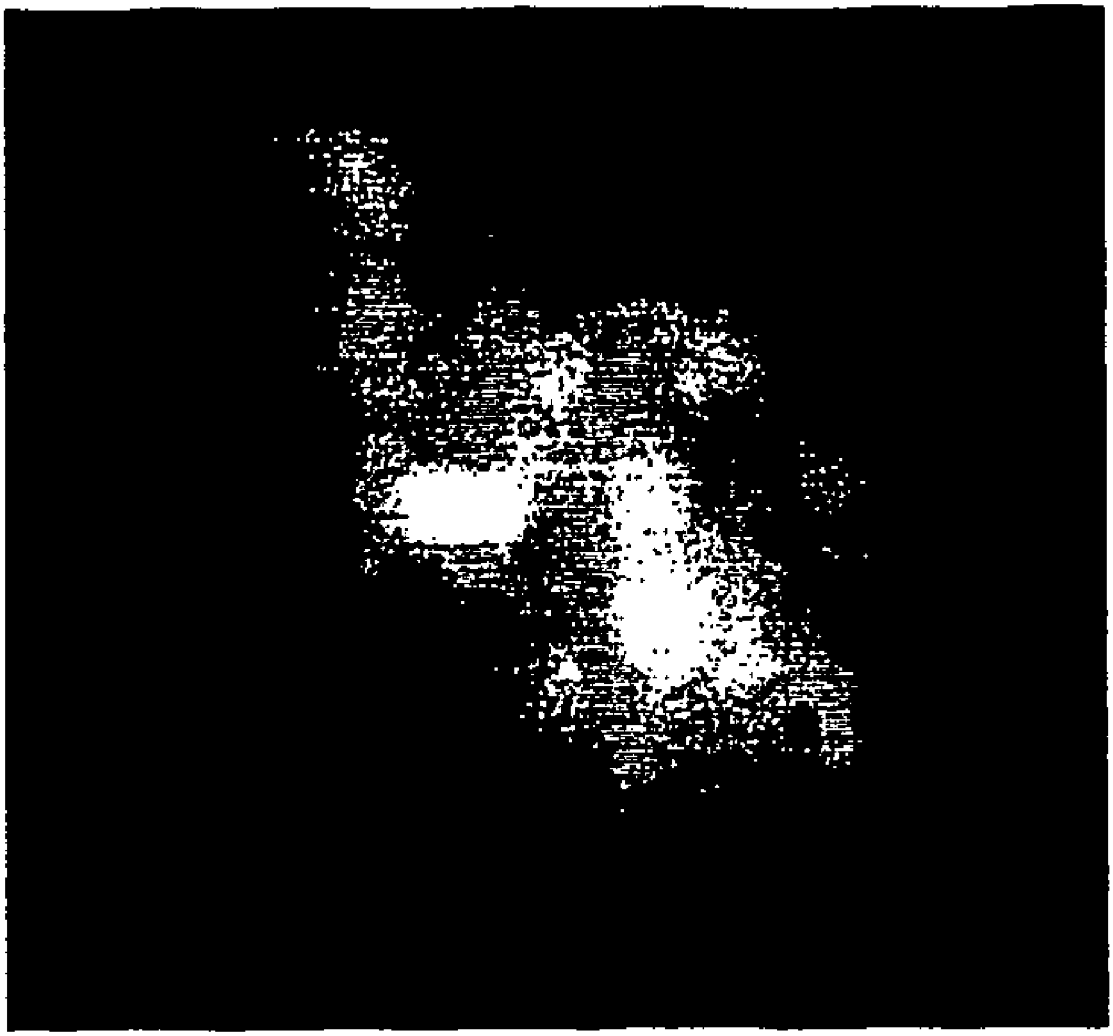
FIG. 4: shows one cell of *P. aeruginosa* with membrane alterations due to treatment with the peptide PS I.

The effect of peptide on the cell membrane of *P. aeuruginosa* was examined under AFM. FIGS. 4 shows image of a intact bacteria and in FIG. 5 one cell of *P aeruginosa* treated by peptides. Peptide was added to bacteria and incubated for 4 hour under the same conditions as in the anti-microbial assay. At the MIC, grooves were developed on the surface of *P. aeuruginosa* indicating that the inhibition of bacterial growth should be associated with the destruction of the bacterial membrane.

The invention claimed is:

1. An isolated antibiotic peptide with broad spectrum anti-microbial activity having the amino acid sequence:

Phe Leu Ser Leu Ile Pro His Ala Ile Asn Ala Val Ser $Xaa^1$ $Xaa^2$ $Xaa^3$ $Xaa^4$ His $Xaa^5$ (SEQ ID NO: 4)

wherein $Xaa^1$, $Xaa^2$, $Xaa^3$, $Xaa^4$ and $Xaa^5$ are each independently a hydrophobic amino acid, a hydrophilic basic amino acid or a hydrophilic neutral amino acid, with the proviso that when $Xaa^2$ and $Xaa^3$ are hydrophobic amino acids, $Xaa^1$ is a hydrophobic amino acid or a hydrophilic neutral amino acid, $Xaa^4$ is a hydrophilic basic amino acid or hydrophilic neutral amino acid, and $Xaa^5$ is a hydrophilic neutral amino acid or hydrophobic amino acid.

2. The isolated antibiotic peptide according to claim 1 wherein the hydrophobic amino acids $Xaa^1$, $Xaa^2$ and $Xaa^3$ are Ala, Ile and Ala, respectively; the hydrophilic basic amino acid $Xaa^4$ is Lys and the hydrophilic neutral amino acid $Xaa^5$ is Asn.

3. The isolated antibiotic peptide according to claim 1 wherein the hydrophobic amino acids $Xaa^2$, $Xaa^3$ and $Xaa^5$ are Leu and Val and Phe, respectively; $Xaa^1$ is Thr; $Xaa^4$ is His.

4. The isolated antibiotic peptide according to claim 1 wherein the hydrophobic amino acids $Xaa^2$, $Xaa^3$ and $Xaa^5$ are Leu, Ala, and Gly, respectively; the hydrophobic amino acid $Xaa^1$ is Ala; and the hydrophilic neutral amino acid $Xaa^4$ is Asn.

5. The isolated antibiotic peptide according to claim 1 wherein the complete polypeptide chain or specific parts of it comprises both α-D- and α-L-amino acid residues.

6. The isolated antibiotic peptide according to claim 1 wherein the complete polypeptide chain or specific parts of it comprises either α-D- or α-L-amino acid residues.

7. A composition for inhibiting growth of a target cell, comprising (a) at least one antibiotic peptide as defined in claim 1, and (b) an acceptable pharmaceutical carrier.

8. The composition according to claim 7 suitable for human or veterinary pharmaceutical use, wherein at least one antibiotic peptide is synthesized manually or on an automatic peptide synthesizer.

9. A composition for retarding plant pathogens and for protecting plants from pathogens, comprising (a) at least one antibiotic peptide as defined in claim 1 and (b) an agriculturally acceptable carrier.

10. An isolated antibiotic peptide with broad spectrum anti-microbial activity, having the same amino acid sequence or at least 74% of similarity with SEQ ID NOS: 1, 2, or 3.

* * * * *

UNITED STATES PATENT AND TRADEMARK OFFICE

CERTIFICATE OF CORRECTION

PATENT NO. : 7,371,720 B2 
APPLICATION NO. : 10/484837
DATED : May 13, 2008
INVENTOR(S) : Genaro Ribeiro De Paiva et al.

It is certified that error appears in the above-identified patent and that said Letters Patent is hereby corrected as shown below:

On the title page, item (57), line 2, "Phyllosepti ns," should read --Phylloseptins,--.

Signed and Sealed this

Twenty-sixth Day of August, 2008

JON W. DUDAS
*Director of the United States Patent and Trademark Office*